(12) United States Patent
Majeed et al.

(10) Patent No.: US 10,716,823 B2
(45) Date of Patent: Jul. 21, 2020

(54) ADAPTOGENIC COMPOSITIONS AND APPLICATIONS THEREOF

(71) Applicants: Muhammed Majeed, Edison, NJ (US); Kalyanam Nagabhushanam, East Windsor, NJ (US)

(72) Inventors: Muhammed Majeed, Edison, NJ (US); Kalyanam Nagabhushanam, East Windsor, NJ (US)

(73) Assignee: SAMI LABS LIMITED, Bangalore (IN)

(*) Notice: Subject to any disclaimer, the term of this patent is extended or adjusted under 35 U.S.C. 154(b) by 542 days.

(21) Appl. No.: 15/051,777

(22) Filed: Feb. 24, 2016

(65) Prior Publication Data

US 2017/0239311 A1 Aug. 24, 2017

(51) Int. Cl.

| | | |
|---|---|---|
| *A61K 36/889* | (2006.01) | |
| *A61K 36/324* | (2006.01) | |
| *A61K 31/7034* | (2006.01) | |
| *A61K 31/715* | (2006.01) | |
| *A61K 36/47* | (2006.01) | |

(52) U.S. Cl.
CPC ........ *A61K 36/889* (2013.01); *A61K 31/7034* (2013.01); *A61K 31/715* (2013.01); *A61K 36/324* (2013.01); *A61K 36/47* (2013.01)

(58) Field of Classification Search
None
See application file for complete search history.

(56) References Cited

U.S. PATENT DOCUMENTS

| | | | | |
|---|---|---|---|---|
| 2005/0192251 A1* | 9/2005 | Banerjee | .............. | A61K 31/736 514/54 |
| 2008/0275117 A1* | 11/2008 | Li | .......................... | A61K 31/19 514/546 |
| 2010/0062989 A1* | 3/2010 | Majeed | .................. | A61K 8/602 514/25 |
| 2011/0218172 A1* | 9/2011 | Majeed | ................ | A61K 31/715 514/54 |

OTHER PUBLICATIONS

Antony et al. (2008) Indian Journal of Clinical Biochemistry, 23(4): 378-381. (Year: 2008).*
Muthuraman et al. (2011) Inflammopharmacol. 19: 327-334. (Year: 2011).*
Nicolis et al. (2008) International Immunopharmacology, 8: 1672-1680. (Year: 2008).*
Reflection Paper on the Adaptogenic Concept, Committee on Herbal Medicinal Products (HMPC), Evaluation of Medicines for Human Use, London, May 8, 2008, Doc. Ref. EMEA/HMPC/102655/2007.
Anju, Bacopa monnieri—a Preliminary Study Evaluating Its Anti-Stress Activity in Swiss Albino Mice, Research Journal of Pharmaceutical, Biological and Chemical Sciences, vol. 2 Issue 4, Oct.-Dec. 2011, pp. 786-794.
Dairy Australia, "Sports Nutrition", Good Health and Nutrition, ABN 60 105 227 987 Level 5, IBM Tower, 60 City Road, Southbank Victoria 3006 Australia.

* cited by examiner

*Primary Examiner* — Terry A McKelvey
*Assistant Examiner* — Russell G Fiebig

(57) ABSTRACT

Disclosed is the adaptogenic activity of boswellic acids-polysaccharide compositions derived from *Boswellia serrata* in combination with either (i) the concentrate of the liquid endosperm of *Cocos nucifera* or (ii) the extract of *Emblica officinalis* fruit standardized to contain 10% w/w and above of 1-O-galloyl-β-D-glucose (β-glucogallin).

2 Claims, 8 Drawing Sheets

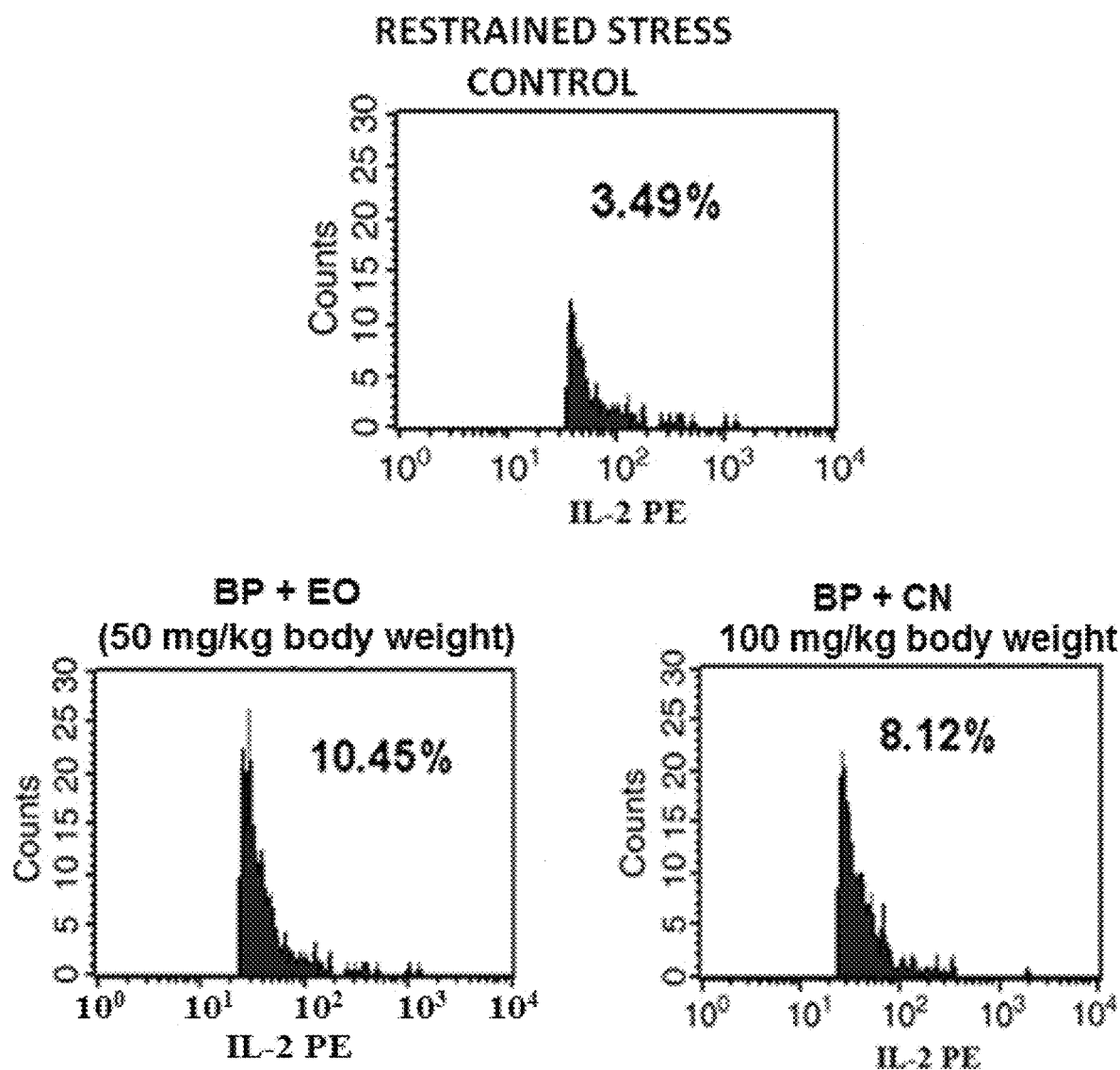

ADAPTOGENIC COMPOSITIONS AND APPLICATIONS THEREOF

FIELD OF INVENTION

The present invention in general relates to the adaptogenic activity of boswellic acids-polysaccharide compositions wherein the polysaccharide component is not less than 70% by weight of the said composition, derived from *Boswellia serrata* in combination with (i) the concentrate of the liquid endosperm of *Cocos nucifera* standardized to contain not less than 70% w/w of total dissolved solids or (ii) the extract of *Emblica officinalis* fruit standardized to contain 10% w/w and above of 1-O-galloyl-β-D-glucose (β-glucogallin) and not more than 5% w/w of gallic acid.

BACKGROUND OF THE INVENTION

Description of Prior Art

Composition comprising boswellic acids and polysaccharides obtained from *Boswellia serrata* and effects therein in terms of down-regulating pro-inflammatory cytokines has been disclosed by Muhammed Majeed et al in U.S. patent application Ser. No. 12/768,871. Similar water-soluble bioactive fraction obtained from the gum resin exudate of *Baswellia serrata* enriched in polysaccharides having applications in anti-inflammatory and anti-arthritic management methods have also been disclosed in U.S. patent application Ser. No. 11/115,823. The present invention discloses adaptogenic activity of boswellic acids-polysaccharide compositions derived from *Boswellia serrata* in combination with (i) the concentrate of the liquid endosperm of *Cocos nucifera* standardized to contain not less than 70% w/w of total dissolved solids or (ii) the extract of *Emblica officinalis* fruit standardized to contain 10% w/w and above of 1-O-galloyl-β-D-glucose (β-glucogallin) and not more than 5% w/w of gallic acid.

While no specific definition of adaptogens exist, the term adaptogens or adaptogenic substances are stated to have the capacity to normalize body functions and strengthen systems compromised by stress. They are reported to have a protective effect on health against a wide variety of environmental assaults and emotional conditions. The role of adaptogens in phytotherapy is best summarized as follows. Most modern active substances are directed to well-defined clinical conditions. If preventive actions are intended, they are specific to a certain disease factor, e.g. vaccines, use of anti-virals, or they are directed to a certain pathological factor with a view to reducing the risk of disease, e.g. cholesterol lowering substances. In contrast to these approaches, the action of adaptogens is reported to be neither directed to eliminate the symptoms of already existing diseases nor is the action specific. If used in an already developed disease, adaptogens are thought to create unspecific effects and in this case they mostly are thought to prevent complications of a disease and to strengthen the general state of the organism. Adaptogens are described to promote non-specific resistance of the body against diseases and different types of stress. This is why a much broader spectrum of action is attributed to adaptogens as compared to most conventional active substances. Nevertheless, the concept of adaptogens is sufficient to be considered in the assessment of traditional herbal medicinal products (REFLECTION PAPER ON ADAPTOGENIC CONCEPT, COMMITTEE ON HERBAL MEDICINAL PRODUCTS (HMPC), European Medicines Agency, Evaluation of Medicines for Human Use, London, 8 May 2008, Doc. Ref. EMEA/HMPC/102655/2007). For example, the adaptogenic effect of ethanolic extract of *Bacopa monnieri* in acute stress mice models has been disclosed in Anju, "*Bacopa monnieri*—a Preliminary Study Evaluating Its Anti-Stress Activity in Swiss Albino Mice". Research Journal of Pharmaceutical, Biological and Chemical Sciences, Volume 2 Issue 4, October-December 2011, pages 786-794.

The importance of Nutrition and supplementation strategies focusing on adaptogenic effects (acute and chronic) like favorable body composition, physical performance, metabolism, endurance, recovery from stress and injury and the maintenance of body homeostasis form the crux of sports nutrition have also been reported in prior art (Dairy Australia, "SPORTS NUTRITION", Good Health and Nutrition, ABN 60 105 227 987 Level 5, IBM Tower, 60 City Road, Southbank Victoria 3006 Australia).

It is thus the principle objective of the present invention to disclose adaptogenic activity of boswellic acids-polysaccharide compositions derived from *Boswellia serrata* in combination with (i) the concentrate of the liquid endosperm of *Cocos nucifera* standardized to contain not less than 70% w/w of total dissolved solids or (ii) the extract of *Emblica officinalis* fruit standardized to contain 10% w/w and above of 1-O-galloyl-β-D-glucose (β-glucogallin) and not more than 5% w/w of gallic acid. The invention describes the tests for adaptogenic properties of said compositions.

The present invention fulfills the aforesaid objectives and provides further related advantages.

SUMMARY OF THE INVENTION

The present invention discloses the adaptogenic activity of boswellic acids-polysaccharide compositions derived from *Boswellia serrata* in combination with (i) the concentrate of the liquid endosperm of *Cocos nucifera* standardized to contain not less than 70% w/w of total dissolved solids or (ii) the extract of *Emblica officinalis* fruit standardized to contain 10% w/w and above of 1-O-galloyl-β-D-glucose (β-glucogallin) and not more than 5% w/w of gallic acid.

Other features and advantages of the present invention will become apparent from the following more detailed description, taken in conjunction with the accompanying images, which illustrate, by way of example, the principle of the invention.

BRIEF DESCRIPTION OF THE DRAWINGS

FIG. 5b is graphical representation of the effects represented in FIG. 5a.

FIG. 6a shows the cytokine IL-2 expression in experimental mice subjected to chronic restraint stress, said mice treated with
(1) 50 mg/kg body weight per orally of boswellic acids-polysaccharide compositions wherein the polysaccharide component is not less than 70% by weight of the said composition, derived from *Boswellia serrata* in combination with the extract of *Emblica officinalis* fruit standardized to contain 10% w/w and above of 1-O-galloyl-β-D-glucose (β-glucogallin) and not more than 5% w/w of gallic acid (i) the concentrate of the liquid endosperm of *Cocos nucifera* standardized to contain not less than 70% w/w of total dissolved solids
(2) 100 mg/kg body weight per orally of boswellic acids-polysaccharide compositions wherein the polysaccharide component is not less than 70% by weight of the said composition, derived from *Boswellia serrata* in combination with the concentrate of the liquid endosperm of *Cocos nucifera* standardized to contain not less than 70% w/w of total dissolved solids; the effect of compositions (1) and (2) herein above as compared with test mice treated with said ingredients alone.

DESCRIPTION OF THE PREFERRED EMBODIMENTS (FIGS. 1-6)

Figure 1:
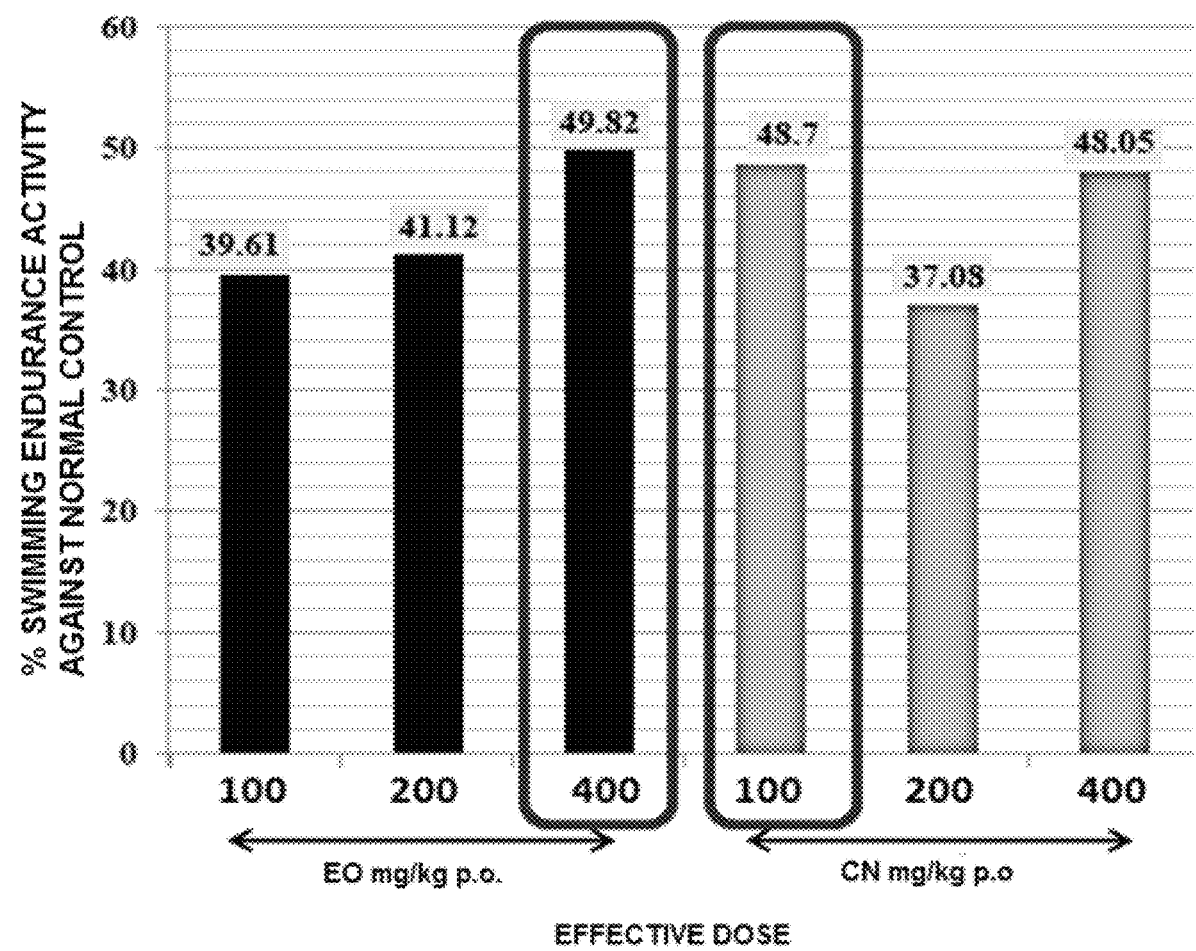
FIG. 1 is a graphical representation of the % enhancement in swimming endurance activity of test animals treated with 100, 200 and 400 mg/kg body weight per orally of concentrate of liquid endosperm of *Cocos nucifera* standardized to contain not less than 70% w/w of total dissolved solids (CN) or the extract of *Emblica officinalis* fruit standardized to contain 10% w/w and above of 1-O-galloyl-β-D-glucose (β-glucogallin) and not more than 5% w/w of gallic acid (EO) as measured in comparison to Normal Control animals.

In the most preferred embodiment, the present invention relates to a method of increasing the physiological endurance of mammals in the event of physical stress, said method comprising step of orally administering effective amounts of compositions (adaptogenic compositions) depending on the body weight of said mammal, wherein said compositions include,
a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;
b) Boswellic acids-polysaccharide compositions derived from *Boswellia serrata* wherein the polysaccharide component is not less than 70%/o by weight of the said composition combined with the extract of *Emblica officinalis fruit standardized to contain 10% w/w and above of 1-O-galloyl-β-D-glucose (β-glucogallin) and not more than 5% w/w of gallic acid.*

In another most preferred embodiment, the present invention relates to a method of protecting against hypoxic injury in mammals during physical stress, said method comprising step of orally administering effective amounts of compositions (adaptogenic compositions) depending on the body weight of said mammal, wherein said compositions include,
a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;
b) Boswellic acids-polysaccharide compositions derived from *Boswellia serrata* wherein the polysaccharide component is not less than 70% by weight of the said composition combined with the extract of *Emblica officinalis* fruit standardized to contain 10% w/w and above of 1-O-galloyl-β-D-glucose (β-glucogallin) and not more than 5% w/w of gallic acid;
to bring about the effect of increased hypoxia induction time.

In yet another most preferred embodiment, the present invention relates to a method of increasing CD3+ T cell subsets (population) in mammals undergoing physical stress and stress induced suppression of cellular immunity, said method comprising step of orally administering effective amounts of compositions (adaptogenic compositions) depending on the body weight of said mammal, wherein said compositions include,
a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;
b) Boswellic acids-polysaccharide compositions derived from *Boswellia serrata* wherein the polysaccharide component is not less than 70% by weight of the said composition combined with the extract of *Emblica officinalis* fruit standardized to contain 10% w/w and above of 1-O-galloyl-β-D-glucose (β-glucogallin) and not more than 5% w/w of gallic acid.

In yet another most preferred embodiment, the present invention relates to a method of increasing systemic interleukin-2 (IL-2) expression in mammals undergoing physical stress and stress induced suppression of cellular immunity, said method comprising step of orally administering effective amounts of compositions (adaptogenic compositions) depending on the body weight of said mammal, wherein said compositions include, a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;

b) Boswellic acids-polysaccharide compositions derived from *Boswellia serrata* wherein the polysaccharide component is not less than 70% by weight of the said composition combined with the extract of *Emblica officinalis* fruit standardized to contain 10% w/w and above of 1-O-galloyl-β-D-glucose (β-glucogallin) and not more than 5% w/w of gallic acid.

In yet another most preferred embodiment, the present invention relates to a method of sustaining neuromuscular coordination in mammals undergoing physical stress, said method comprising step of orally administering effective amounts of compositions (adaptogenic compositions) depending on the body weight of said mammal, wherein said compositions include, (a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;

(b) Boswellic acids-polysaccharide compositions derived from *Boswellia serrata* wherein the polysaccharide component is not less than 70% by weight of the said composition combined with the extract of *Emblica officinalis* fruit standardized to contain 10% w/w and above of 1-O-galloyl-β-D-glucose (β-glucogallin) and not more than 5% w/w of gallic acid.

In yet another most preferred embodiment, the present invention also relates to a method of treating stress induced immunosuppressive effects in mammalian spleen, thymus and adrenal glands leading to undesirable atrophy or hypertrophy, said method comprising step of orally administering effective amounts of compositions (adaptogenic compositions) depending on the body weight of said mammal, wherein said compositions include, (a) Boswellic acids-polysaccharide (BP) compositions derived from *Boswellia serrata* wherein the polysaccharide component is not less than 70% by weight of the said composition combined with the concentrate of the liquid endosperm of *Cocos nucifera* standardized to contain not less than 70% w/w of total dissolved solids;

(b) Boswellic acids-polysaccharide compositions derived from *Boswellia serrata* wherein the polysaccharide component is not less than 70% by weight of the said composition combined with the extract of *Emblica officinalis* fruit standardized to contain 10% w/w and above of 1-O-galloyl-β-D-glucose (β-glucogallin) and not more than 5% w/w of gallic acid to bring about the effect of attenuating said stress induced atrophy of spleen and thymus glands and hypertrophy of adrenal glands.

The aforesaid most preferred embodiments are elucidated herein below as illustrative examples.

The acute oral safety study was carried out following OECD guidelines No. 423. A single dose of the test material (s) BP, EO and CN was administered to a group of three females each up to a dose level of 2000 mg/kg. The animals were observed for any gross behavioural changes, for a total of 14 days. No change in general behaviour or any mortality was observed in groups of animals treated by different doses of the test material for 14 days. For the pharmacological studies, the Applicants tested graded doses ranging from 50 mg/kg to 800 mg/kg of the individual extracts BP, CN and EO to calculate the most effective dose for the individual extracts in the Swimming endurance test (procedure discussed herein below) (FIG. 1. The effective doses include BP: 200 mg/kg, EO: 400 mg/kg and CN: 100 mg/kg. Combination of BP (200)+CN (100) was then tested at 50, 100 and 200 mg/kg for swimming endurance and the most effective dose of the combination was achieved at 100 mg/kg. Similarly, Combination of BP (200)+EO (400) was then tested at 50, 100 and 200 mg/kg for swimming endurance and the most effective dose of the combination was achieved at 50 mg/kg. The testing procedures are further described in detail in EXAMPLE I presented herein below.

Figure 2:
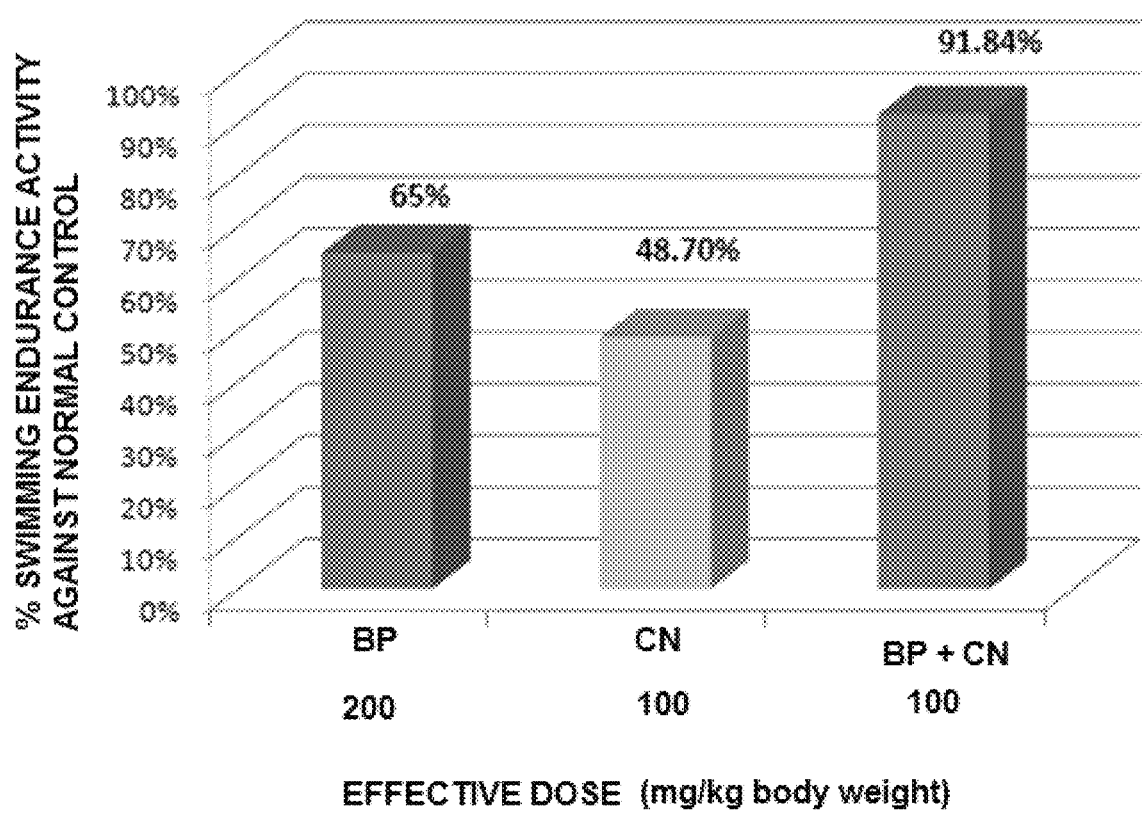
FIG. 2 is a graphical representation of % enhancement in swimming endurance activity of test animals treated with 100 mg/kg body weight per orally of combined ingredients comprising boswellic acids-polysaccharide (BP) compositions wherein the polysaccharide component is not less than 70% by weight of the said composition, derived from *Boswellia serrata* in combination with the concentrate of the liquid endosperm of *Cocos nurcifera* standardized to contain not less than 70% w/w of total dissolved solids as compared with test animals treated with individual ingredients BP (200 mg/kg body weight) and CN (100 mg/kg body weight).
Figure 3:
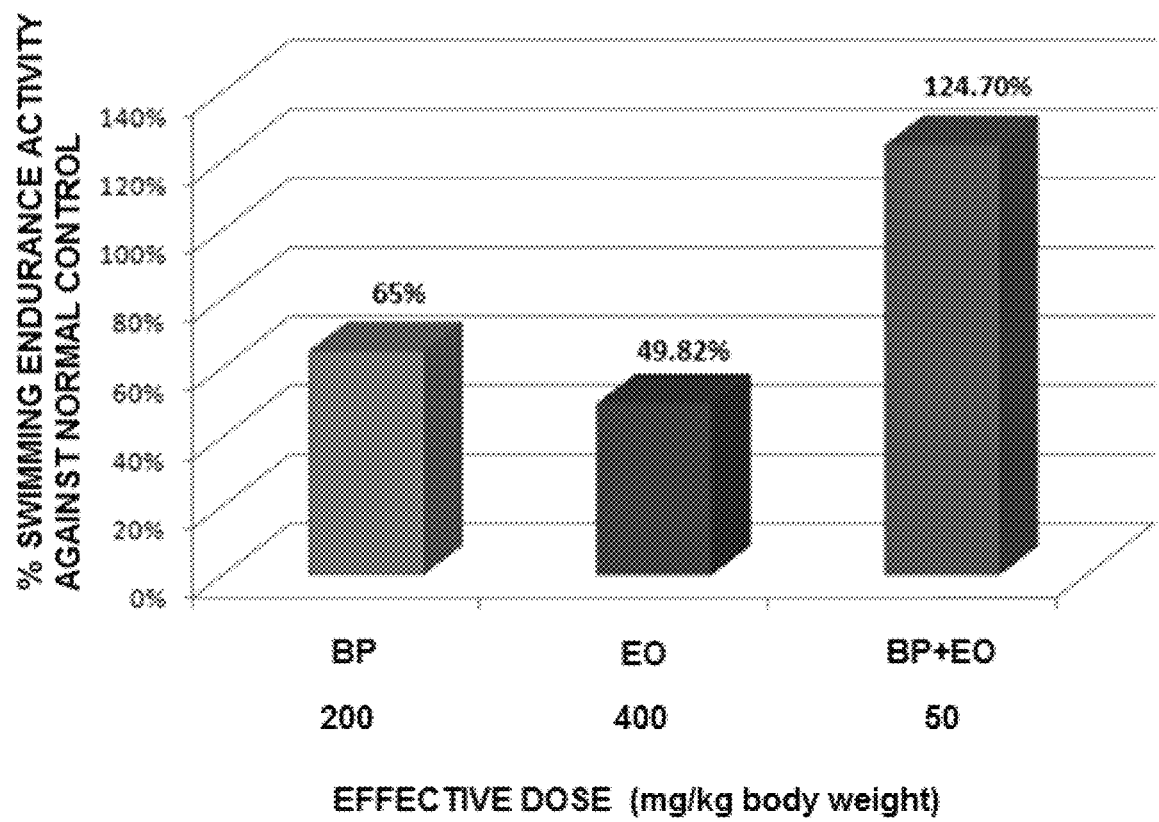
FIG. 3 is a graphical representation of % enhancement in swimming endurance activity of test animals treated with 50 mg/kg body weight boswellic acids-polysaccharide compositions wherein the polysaccharide component is not less than 70% by weight of the said composition, derived from *Boswellia serrata* in combination with the extract of *Emblica officinalis* fruit standardized to contain 10% w/w and above of 1-O-galloyl-β-D-glucose (β-glucogallin) and not more than 5% w/w of gallic acid as compared with test animals treated with individual ingredients BP (200 mg/kg body weight) and EO (50 mg/kg body weight).

Example I—Swimming Endurance (Endurance to Physical Stress) Test (FIGS. 1, 2 and 3)

Animals: Male Swiss albino mice
Weight: 25-30 g
Number of animals per group: 06
Test groups are represented in the following table

| Test Group | Characterization |
| --- | --- |
| Group I (Normal control) | Without swimming stress |
| Group II | Swimming stress control group |
| Group III | (BP + CN)-Adaptogenic composition: 100 mg/kg body weight per oral administration |
| Group IV | (BP + EO)-Adaptogenic composition: 50 mg/kg body weight per oral administration |

Test materials BP, CN and EO formulated as adaptogenic compositions mentioned herein above (Group III and Group IV) were administered per orally to Swiss albino mice (25-30 g) of either sex once a day for 14 days. On day 15, one hour after drug administration, the swimming time of each animal was measured individually by the Swimming Endurance Test. The animals were allowed to swim inside a perplex glass beaker (30 cm high with 20 cm diameter, containing water up to 25 cm height) maintained at 26±1° C. The mice were allowed to swim till they got exhausted which was considered as the endpoint. The mean swimming time for each group was calculated (FIG. 2 for group III and FIG. 3 for group IV). Both (BP+CN)-Adaptogenic composition: 100 mg/kg body weight per oral administration (Group III) and (BP+EO)-Adaptogenic composition: 50 mg/kg body weight per oral administration (Group IV) were very effective in increasing the endurance capacity of test animals in the Swimming Endurance test.

Example II A—Anti-Fatigue Effect

Animals: Swiss albino mice of either sex
Weight: 25-30 g

No. of animals per group: 10
Test groups included the following.

| | |
|---|---|
| Group I (Normal control) | Without swimming stress |
| Group II | Swimming stress control group |
| Group III | (BP + CN)-Adaptogenic composition: 100 mg/kg body weight per oral administration |
| Group IV | (BP + EO)-Adaptogenic composition: 50 mg/kg body weight per oral administration |

Test material was administered orally once a day for 14 days to animal groups III and IV. On day 15, one hour after drug administration in groups III and IV, the animals were allowed to swim inside a perplex glass beaker (30 cm high with 20 cm diameter, containing water up to 25 cm height) maintained at 26±1° C. The mice were allowed to swim till they got exhausted which was considered as the endpoint. Group I animals were not exposed to the swimming stress test. Group II animals were exposed to the swimming endurance test as mentioned above without being administered test materials. Only pre-trained test mice which stayed on a rotating red at 20 rpm, for more than 5 minutes in three successive trials for 5 consecutive days, were used in this study. On day 15, the animals of Group II, III and IV that underwent swimming stress were immediately taken out, dried with tissue paper and placed on the rotating rod to monitor anti-fatigue and motor coordination effects. The number of mice that stayed on the rota-rod for 180 seconds or more were considered as un tired with motor coordination. The percent effect of each group was calculated on the basis of the number of mice that stayed on the rota-rod for >180 seconds (by all or non-method). The same animals were again placed on the rota-rod after 30 minutes of removal from the swimming bath, to monitor the anti fatigue effect once again. Similarly, the animals of Group I which were not allowed to swim were also placed on the rotating rod to see the anti fatigue effect in normal animals. The results of the Anti-fatigue effect testing (neuromuscular coordination) are represented below in Table A.

TABLE A

| TREATMENT | No of animals that stayed on the rod for >180 seconds/total no of animals in the group |
|---|---|
| Group I (No stress control) without any test material treatment | 6/10 |
| Group II (stress control) without any test material treatment | 2/10 |
| Group III (BP + CN)-Adaptogenic composition: 100 mg/kg body weight per oral administration | 8/10 |
| Group IV (BP + EO)-Adaptogenic composition: 50 mg/kg body weight per oral administration | 7/10 |

Figure 4:
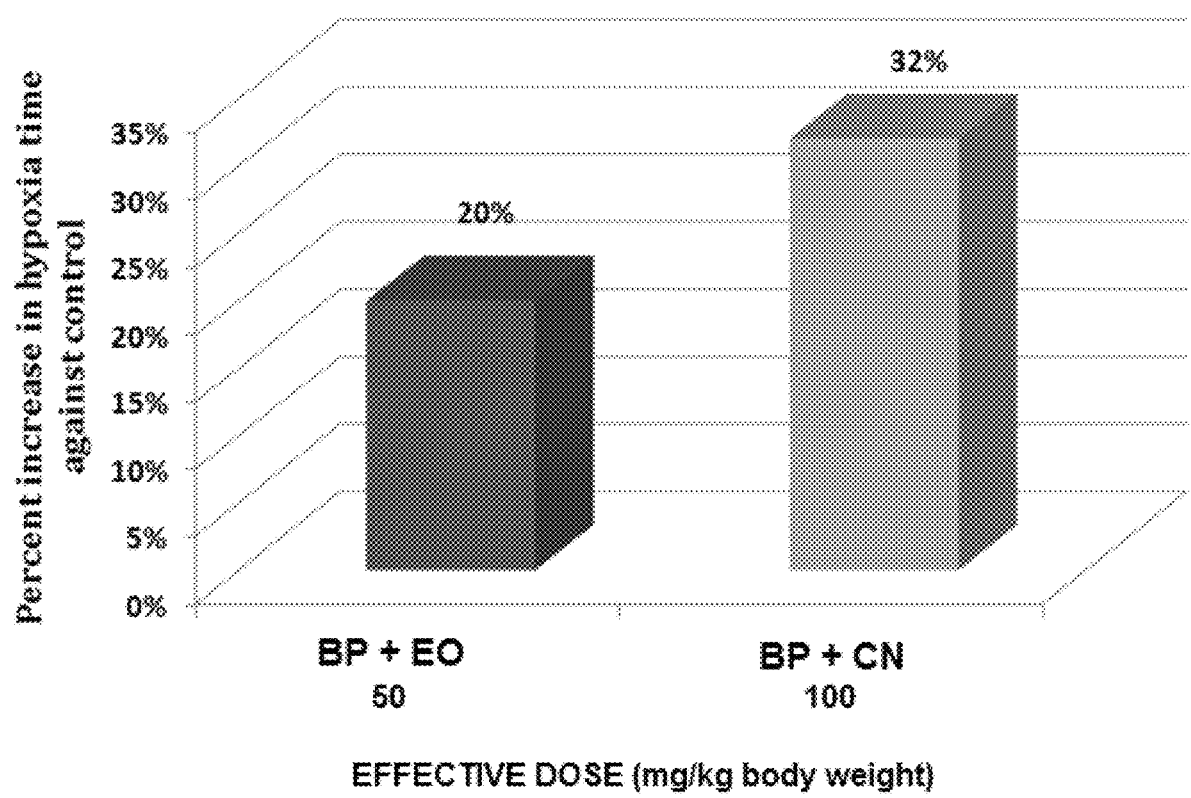
FIG. 4 is graphical representation of % increase in hypoxia induction time against control, of test animals treated with 50 mg/kg body weight per orally of boswellic acids-polysaccharide compositions wherein the polysaccharide component is not less than 70% by weight of the said composition, derived from *Boswellia serrata* in combination with the extract of *Emblica officinalis* fruit standardized to contain 10% w/w and above of 1-O-galloyl-β-D-glucose (β-glucogallin) and not more than 5% w/w of gallic acid or 100 mg/kg body weight per orally of boswellic acids-polysaccharide compositions wherein the polysaccharide component is not less than 70% by weight of the said composition, derived from *Boswellia serrata* in combination with the concentrate of the liquid endosperm of *Cocos nucifera* standardized to contain not less than 70% w/w of total dissolved solids as compared with test animals treated with said ingredients alone during recovery against hypoxia.

Example 2B—Measurement of Hypoxia Time (FIG. 4)

3 groups of test animals (Swiss albino mice of either sex; Weight: 25-30 g and number of animals per group: 10) where Group I includes animals without any test material treatment, Group II animals administered (BP+CN)-Adaptogenic composition: 100 mg/kg body weight per oral administration for 15 days and Group III animals administered (BP+EO)-Adaptogenic composition: 50 mg/kg body weight per oral administration animals for 15 days were tested for their ability for resist hypoxia induction. On day 15, one hour after treatment, the hypoxia time was recorded individually or each animal by placing the animal in an empty glass jar of 300-ml capacity attached to an electronic watch. The jars were made air-tight with greased glass stoppers and the time until onset of convulsion was recorded as the end point. The results of the hypoxia induction time testing are represented in FIG. 4. The graphs indicate that percentage hypoxia induction time was enhanced for Group II (32%) and Group III (20%) as compared to control untreated Group 1.

Example 3—Chronic Restraint Stress Test

Figure 5A:
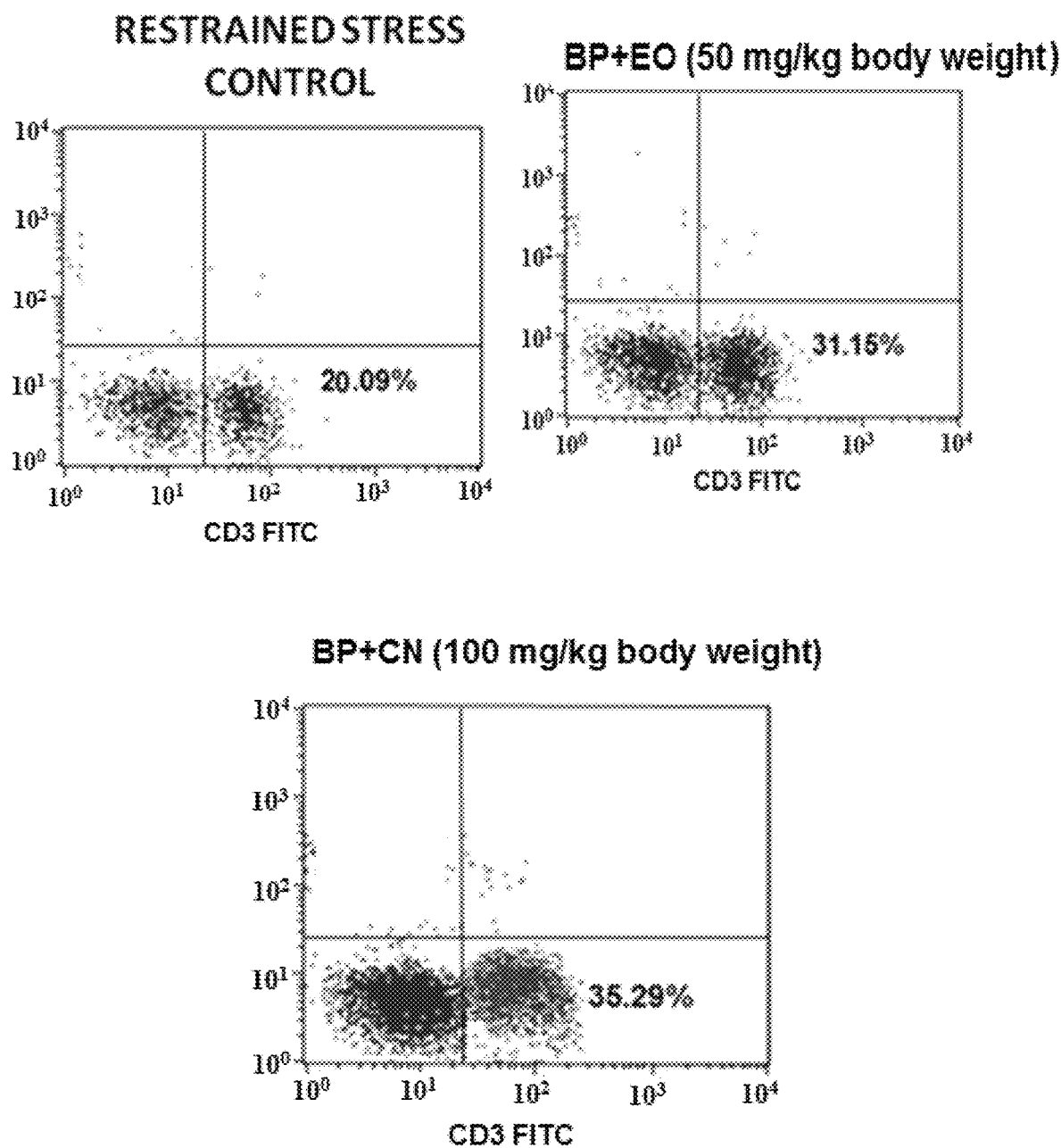
FIG. 5a shows the expression of increase in CD3+ T cell expression in experimental mice subjected to chronic restraint stress, said mice treated with
(1) 50 mg/kg body weight per orally of boswellic acids-polysaccharide compositions wherein the polysaccharide component is not less than 70% by weight of the said composition, derived from *Boswellia serrata* in combination with the extract of *Emblica officinalis* fruit standardized to contain 10% w/w and above of 1-O-galloyl-β-D-glucose (β-glucogallin) and not more than 5% w/w of gallic acid;
(2) 100 mg/kg body weight per orally of boswellic acids-polysaccharide compositions wherein the polysaccharide component is not less than 70% by weight of the said composition, derived from *Boswellia serrata* in combination with the concentrate of the liquid endosperm of *Cocos nucifera* standardized to contain not less than 70% w/w of total dissolved solids); the effect of compositions (1) and (2) herein above as compared with test mice treated with said ingredients alone.
Figure 5B:
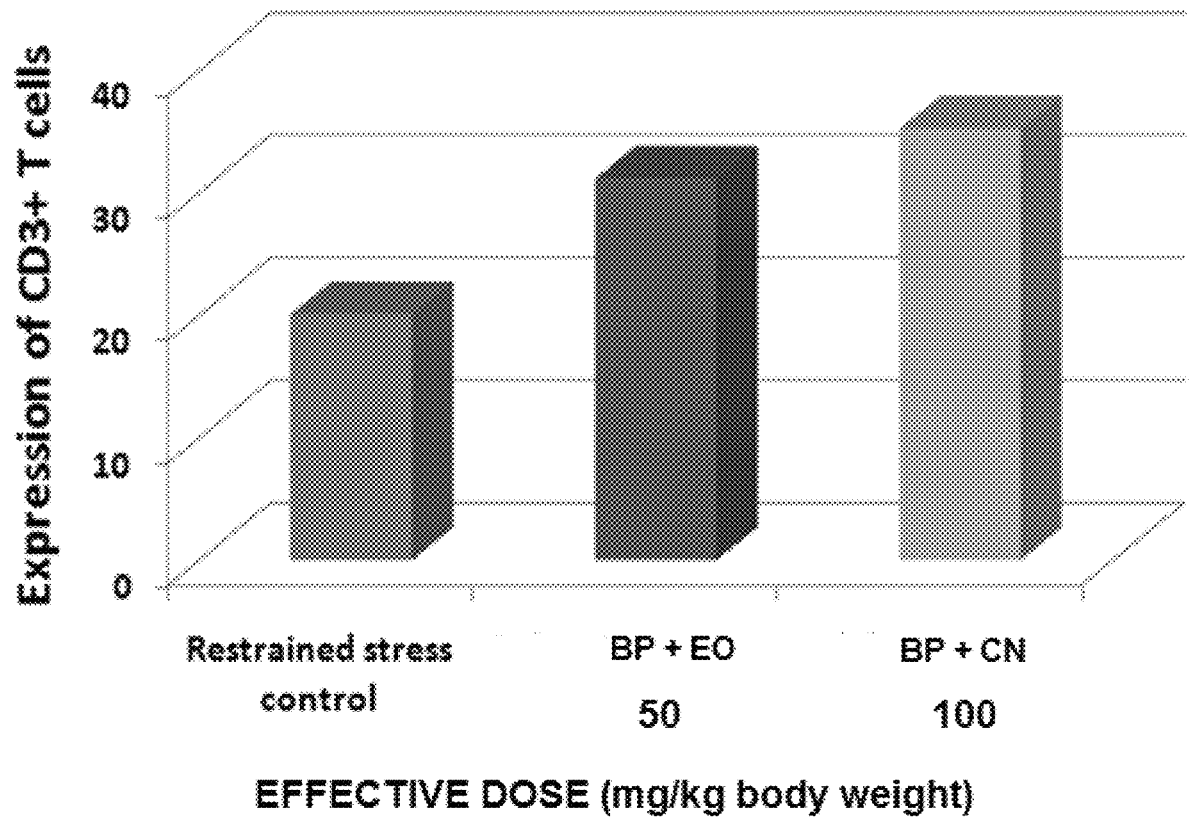
Figure 6B:
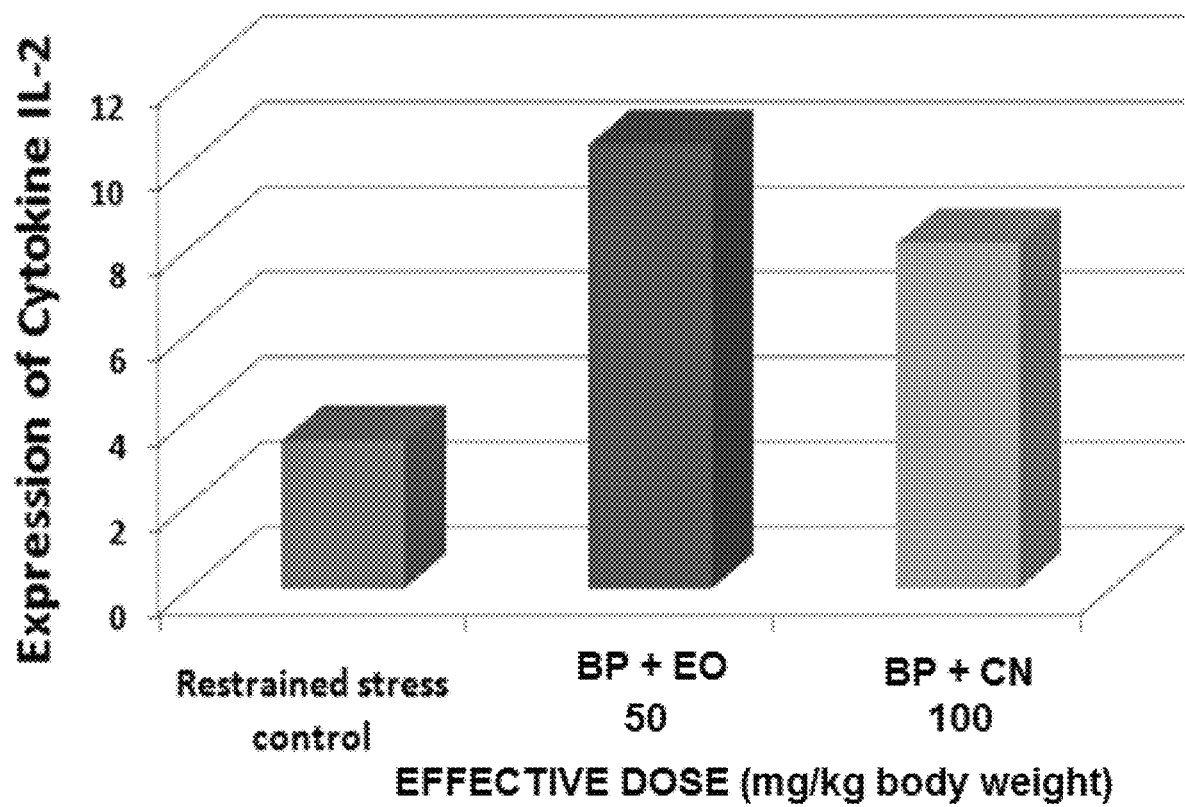
FIG. 6b is a graphical representation of the effects represented in FIG. 6.

Male Swiss albino mice, 10-12 weeks old and weighing about 20-22 grams were employed for this study. Mice were restrained in these 50 ml conical polypropylene tubes for 12 h during the dark cycle (2000-0800 h) for 14 days. Experimental animals were divided into groups of eight animals each. Group-I served restraint stress control group without treatment with test material. Group-II included animals treated with (BP+EO)-Adaptogenic composition: 50 mg/kg body weight per oral administration for 15 days and subjected to the chronic restraint stress test as described before. Group III included animals treated (BP+CN)-Adaptogenic composition: 100 mg/kg body weight per oral administration. Following the chronic restraint stress procedure, lymphocyte immunotyping to evaluate suppression of cellular immunity due to stress was done. Blood was taken from the retro-orbital plexus of animals from all the groups for the assessment of various immune cells surface markers. Murine anti-CD3+ monoclonal antibodies were used in a multi parametric flowcytometric assay to quantify the lymphocyte subsets associated with the cell-mediated immune response. These flourochrome labeled monoclonal antibodies were added directly to 100 µl of whole blood, which was then lysed using whole blood lysing reagent (BD Biosciences). Following the final centrifugation, samples were resuspended in phosphate buffer saline (pH, 7.4) and analyzed directly on the flowcytometer (BD Biosciences) using Cell Quest Pro Software (BD Biosciences) (FIG. 5a). FIG. 5a shows 20.09% CD3+T lymphocyte subsets in the restrained stress control group. Group 11 and III treated groups show 31.15% and 35.29% CD3+T lymphocyte subsets indicating recovery of cellular immunity. Further, intracellular cytokine IL-2 levels were estimated in blood by flowcytometry using Phycoerythrin (PE) labeled IL-2 monoclonal antibodies. Acquisition and the analysis were done directly on flowcytometer using Cell Quest Pro software (BD Biosciences). Chronic restrained stress condition suppressed the expression of IL-2 to 3.49% in Group I-restraint stress control group. The % IL-2 expression increased in Groups II and III to 10.45% and 8.12%.

Example IV—Body and Organ Weights

After the last stress session, the body weights of all the animals from all the groups were taken following which the animals were sacrificed and their thymus, adrenal glands, and spleen, were removed and weighed. Table B indicates that (BP+CN)-Adaptogenic composition: 100 mg/kg body weight per oral administration and (BP+EO)-Adaptogenic composition: 50 mg/kg body weight per oral administration attenuated stress induced atrophy of spleen and thymus glands and hypertrophy of adrenal glands.

TABLE B

| TREATMENT | Thymus (mg) | Spleen (mg) | Adrenal glands (mg) |
|---|---|---|---|
| Normal control | 650.28 ± 1.2 | 720.12 ± 1.1 | 13.60 ± 0.9 |
| Restraint Stress control | 310.29 ± 1.2 | 390.25 ± 1.9 | 38.65 ± 1.3 |
| (BP + CN)-Adaptogenic composition: 100 mg/kg body weight per oral administration | 418.45 ± 1.4 (34.85↑) | 456.72 ± 1.9 (17.03↑) | 29.35 ± 2.4 (24.06↓) |
| (BP + EO)-Adaptogenic composition: 50 mg/kg body weight per oral administration | 480.11 ± 2.1 (53.75↑) | 530.21 ± 2.2 (35.86↑) | 23.52 ± 1.2 (39.14↓) |

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of increasing physiological endurance in mammals subjected to strenuous physical activity, comprising a step of orally administering an effective amount of a composition consisting of:
   (a) 1 part Boswellic acids-polysaccharide (BP) extract derived from *Boswellia serrata*, wherein the extract contains is not less than 70% polysaccharides, and
   (b) 2 parts *Emblica officinalis* (EO) fruit extract standardized to contain at least 10% w/w and of 1-O-galloyl-β-D-glucose (β-glucogallin) and not more than 5% w/w of gallic acid,
   wherein the composition is administered once a day for a sufficient duration to bring about an increase in physiological endurance, and
   wherein the effective amount is 50 mg/kg body weight of the mammal.

2. A method of increasing physiological endurance in mammals subjected to strenuous physical activity, comprising a step of orally administering an effective amount of a composition consisting of:
   (a) 2 parts Boswellic acids-polysaccharide (BP) extract derived from *Boswellia serrata*, wherein the extract contains is not less than 70% polysaccharides, and
   (b) 1 part concentrate of the liquid endosperm of *Cocos nucifera* (CN), once a day, to bring about an increase in physiological endurance,
   wherein the composition is administered once a day for a sufficient duration to bring about an increase in physiological endurance, and
   wherein the effective amount is 100 mg/kg body weight of the mammal.

* * * * *